(12) United States Patent
Weisshaupt et al.

(10) Patent No.: US 12,349,960 B2
(45) Date of Patent: Jul. 8, 2025

(54) ELECTROSURGICAL COAGULATION INSTRUMENT

(71) Applicant: Aesculap AG, Tuttlingen (DE)

(72) Inventors: Dieter Weisshaupt, Immendingen (DE); Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 1308 days.

(21) Appl. No.: 15/575,621

(22) PCT Filed: May 13, 2016

(86) PCT No.: PCT/EP2016/060813
§ 371 (c)(1),
(2) Date: Nov. 20, 2017

(87) PCT Pub. No.: WO2016/184796
PCT Pub. Date: Nov. 24, 2016

(65) Prior Publication Data
US 2018/0153613 A1 Jun. 7, 2018

(30) Foreign Application Priority Data
May 21, 2015 (DE) ...................... 10 2015 108 078.8

(51) Int. Cl.
*A61B 18/14* (2006.01)
*A61B 17/00* (2006.01)
*A61B 18/00* (2006.01)

(52) U.S. Cl.
CPC .. *A61B 18/1445* (2013.01); *A61B 2017/0088* (2013.01); *A61B 2018/00083* (2013.01);
(Continued)

(58) Field of Classification Search
CPC ..................... A61B 18/1445; A61B 2017/0088
See application file for complete search history.

(56) References Cited

U.S. PATENT DOCUMENTS 8,469,956 B2 * 6/2013 McKenna .......... A61B 18/1482
606/51
2001/0041893 A1 11/2001 Bartel
(Continued)

FOREIGN PATENT DOCUMENTS

CN 1889886 A 1/2007
CN 103327922 A 9/2013
(Continued)

OTHER PUBLICATIONS

German Search Report for German Application No. 10 2015 108 078.8, with translation, dated Jan. 19, 2016—15 Pages.
(Continued)

*Primary Examiner* — Linda C Dvorak
*Assistant Examiner* — Ryan T Clark
(74) *Attorney, Agent, or Firm* — Christopher A. Rothe; CM Law

(57) ABSTRACT

An electrosurgical instrument for the electrocoagulation of tissue includes a jaw part which has two instrument branches. At least one instrument branch is movable in relation to the other instrument branch such that the jaw part can be brought into an open position or into a closed position. Facing sides of the instrument branches, respectively intended as grip faces, are configured for the clamping hold of tissue to be coagulated in the closed position. Each instrument branch has at least one electrode face. The grip faces have an electrically insulating design. Each electrode face is arranged in the grip face of the respective instrument branch and is recessed in the grip face on at least one of the instrument branches.

20 Claims, 1 Drawing Sheet

(52) U.S. Cl.
CPC ............ *A61B 2018/00136* (2013.01); *A61B 2018/00494* (2013.01); *A61B 2018/00589* (2013.01); *A61B 2018/0063* (2013.01)

(56) References Cited

U.S. PATENT DOCUMENTS

| | | | |
|---|---|---|---|
| 2003/0018331 A1* | 1/2003 | Dycus | A61B 18/1445 606/51 |
| 2003/0216733 A1 | 11/2003 | McClurken et al. | |
| 2004/0116979 A1 | 6/2004 | Truckai et al. | |
| 2004/0122423 A1 | 6/2004 | Dycus et al. | |
| 2008/0294222 A1* | 11/2008 | Schechter | A61B 18/1445 607/50 |
| 2009/0177070 A1 | 7/2009 | Bernhart et al. | |
| 2010/0100122 A1 | 4/2010 | Hinton | |
| 2011/0064881 A1 | 3/2011 | Zimmerman et al. | |
| 2011/0098700 A1* | 4/2011 | Tamai | A61B 18/1445 606/41 |
| 2012/0283735 A1 | 11/2012 | Schechter | |
| 2012/0296325 A1 | 11/2012 | Takashino | |
| 2012/0323234 A1 | 12/2012 | Weisshaupt et al. | |
| 2014/0142574 A1 | 5/2014 | Heard | |
| 2014/0214025 A1 | 7/2014 | Worrell et al. | |
| 2014/0288552 A1 | 9/2014 | Kunis et al. | |
| 2014/0288553 A1 | 9/2014 | Johnson et al. | |
| 2014/0309635 A1 | 10/2014 | Lutze et al. | |
| 2014/0371743 A1 | 12/2014 | Rothweiler et al. | |
| 2015/0250530 A1 | 9/2015 | Manzo et al. | |
| 2015/0374430 A1* | 12/2015 | Weiler | A61B 18/1445 606/46 |
| 2016/0045770 A1 | 2/2016 | Yamada | |

FOREIGN PATENT DOCUMENTS

| | | |
|---|---|---|
| CN | 103813762 A | 5/2014 |
| DE | 202008004064 U1 | 7/2008 |
| DE | 202010013150 U1 | 3/2011 |
| DE | 102012100040 A1 | 7/2013 |
| EP | 1151723 A2 | 11/2001 |
| EP | 1372507 A1 | 1/2004 |
| EP | 1656901 A1 | 5/2006 |
| EP | 1372507 B1 | 6/2006 |
| EP | 1747762 A2 | 1/2007 |
| EP | 1952777 A1 | 8/2008 |
| EP | 2491880 A1 | 8/2012 |
| WO | 9725917 A1 | 7/1997 |
| WO | 2011064881 A1 | 6/2011 |
| WO | 2015029518 A1 | 3/2015 |

OTHER PUBLICATIONS

International Search Report and Written Opinion for International Application No. PCT/EP2016/060813, dated Jul. 26, 2016—9 Pages.
Japanese Notification of Reasons for Rejection for Japanese Application No. 2017-560582, dated Mar. 3, 2020 with 1 translation, 9 pages.
Chinese Office Action and Search Report CN Application No. 202003120127820 dated Mar. 17, 2020, 31 pages.
Chinese Office Acton received in Application No. 201680037332.4 mailed Nov. 16, 2020, 29 pages.

* cited by examiner

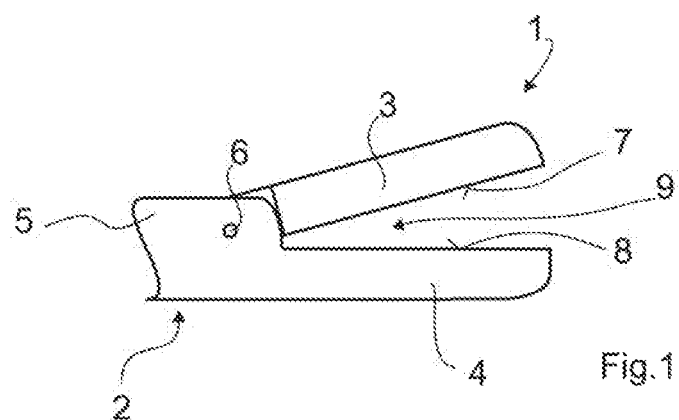
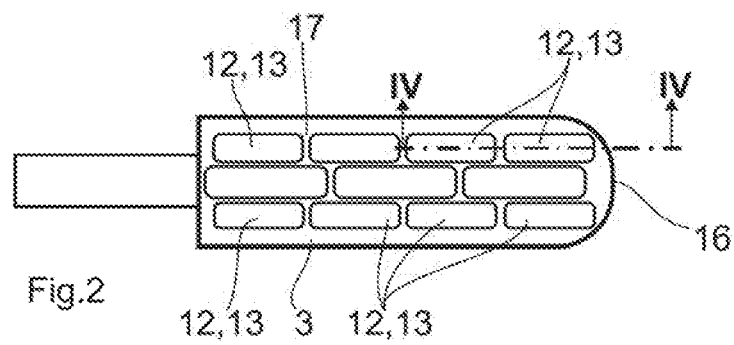
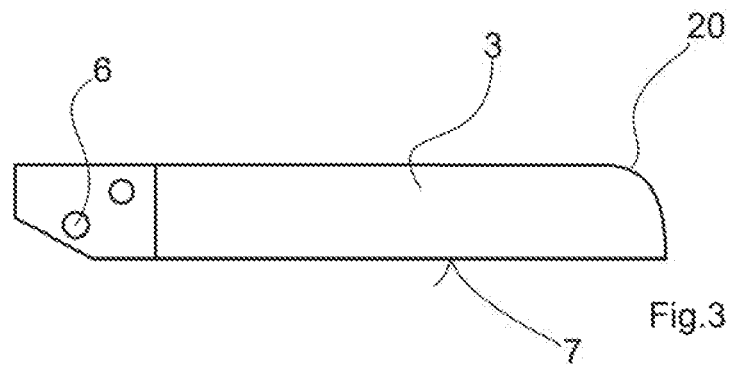
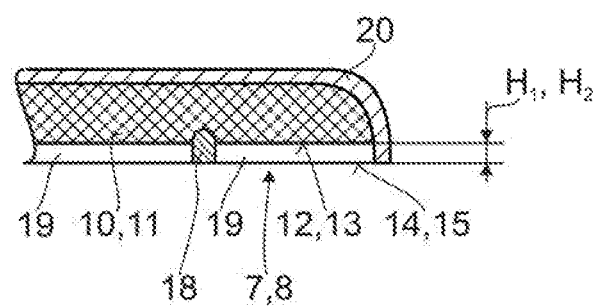

ELECTROSURGICAL COAGULATION INSTRUMENT

RELATED APPLICATIONS

This application is the U.S. national phase entry of International Application No. PCT/EP2016/060813, filed May 13, 2016, which is related to and claims the benefit of priority of German Application No. 10 2015 108 078.8, filed May 21, 2015. The contents of International Application No. PCT/EP2016/060813 and German Application No. 10 2015 108 078.8 are incorporated by reference herein in their entireties.

The present invention relates to an electro surgical instrument for electrocoagulation of tissue, comprising a jaw part which has two instrument branches or clamping, jaws of which at least one is movable in relation to the other one such that the jaw part can be brought into an opened position or into a closed position, wherein facing sides, especially inner surfaces, of the instrument branches, respectively intended as grip faces, are configured for the clamping hold therebetween of tissue to be coagulated in the closed position and each have at least one electrode face.

BACKGROUND

A powerful alternative to the tissue connection consists in coagulating tissue by HF current (high-frequency current), for example by applying HF current between two HF electrodes to the tissue. The application of HF current at least partially entails denaturation of tissue proteins, wherein e.g. triple-helical collagen, which is a major component of connective tissue, is disintegrated in collagenic individual helices. The denatured protein components can be easily merged achieving a tissue connection.

For welding tissue, current flowing between electrodes of the jaws/branches is applied to tissue caught between two clamping jaws or instrument branches. In order to prevent the sealing or welding from failing, parameters acting on the tissue and being present during welding have to be detected and controlled. For ensuring this step, an exact control of temperature, pressure, tissue impedance as well as distance and position of the electrodes is required.

It is desirable to treat tissue held between the clamping jaws in a uniform manner so that all areas are reliably reached and excessive current is applied to none of them. It has to be safeguarded for this purpose that the HF electrodes are spaced evenly apart from each other and, resp., are aligned in parallel to each other.

From prior art, coagulation instruments of smaller design are known, as shown e.g. in EP 1 747 762 A2, in which, due to the constructional design, a non-parallel alignment of the HF electrodes may occur when closing the clamping jaws, for example by virtue of deflection. This results in a reduction of the distance between the electrodes, in the most unfavorable case short-circuits may occur.

It is known to comply with the distance between electrodes of a coagulation instrument by spacers disposed between the electrodes. When, however, a larger number of spacers is provided on the clamping jaws, as is shown e.g. in EP 1 656 901 B1, EP 1 952 777 A1, EP 1 172 507 A1 or U.S. 2004/122423 A1, the spacers necessarily perforate the tissue to be treated, as the tissue beneath the spacers is compressed when the clamping jaws are closed so that permanent damage of the tissue will occur. This has adverse effects on the result of sealing.

Since the spacers furthermore are made from electrically non-conductive material so as to avoid short-circuit between the HF electrodes, in the area of said spacers a so-called coagulation shadow is formed, that is to say the tissue sections are encapsulated in the area of or beneath the spacers and thus no or only insufficient current is applied to them and the vessel sections are not satisfactorily welded there. Moreover, it has turned out that those electrically non-conductive spacers may easily come off, especially when they are fastened to the electrode by gluing, for example, and then may enter possibly unnoticed into a patient's body. In addition, in such case the predefined electrode distance is no longer guaranteed.

Summing up, it can be stated that in known instruments for HF sealing of tissue possibly short-circuits may occur, which usually has a negative influence on the result of coagulation and moreover may promote adhesions of tissue to the electrodes. Spacers arranged between the electrodes or, resp., the electrode faces likewise deteriorate the result of coagulation. Especially at electrode corners there may occur concentrations of current which may equally have a negative influence on the result, of coagulation. Electrodes, that are not electrically insulated cause collateral damage to the tissue.

SUMMARY

Against this background, the object underlying the present invention is to provide an instrument which enables reproducible sealing of tissue, especially of human tissue, by means of thermal fusion technology, wherein electric short-circuits of the electrodes are safely avoided and adhesions of tissue to the electrodes can be reduced and, resp., avoided. Moreover, collateral damage to the tissue is intended to be avoided or reduced by electrically non-conductive jaw parts such as separate spacers. The instrument is generally intended to be suited for tissue connections, inter alia for end-to-end anastomosis of hollow vessels such as small and large intestines.

This object is achieved, according to the present invention, by an electrosurgical instrument, especially a bipolar instrument. In particular, at least one of the electrode faces is arranged in or inside the grip face located on the same instrument branch and is sunk in relative thereto. The grip faces and, resp., a structure including or forming the same is made especially from electrically insulating material.

It can also be stated that by the invention the electrode face is arranged or formed to be recessed vis-à-vis the grip face of the respective instrument branch. It is offset in a direction facing away from the opposite instrument branch. As a result, in the closed state of the two branches each electrode face of the one instrument branch is spaced apart from each electrode face of the other instrument branch, while the grip faces protrude and form the mutual contacting options of the branches. At least one of the grip faces in this way forms a spacer between the instrument branches so that no short-circuit is possible between the electrodes of the branches. This spacer is advantageously arranged outside the electrode face so that the coagulation is not adversely affected. Other than in the case of known instruments in which tissue to be coagulated is retained and clamped by means of the electrode faces which are kept distanced by means of separately provided insulating spacers, in an instrument according to the invention the electrically insulating grip faces retain and clamp tissue to be coagulated. The grip faces and, resp., the structure configuring the latter may advantageously form the load-bearing elements of the branches or are supported by them and absorb forces and moments introduced by the tissue when tissue is clamped. In the invention, the electrodes forming the electrode faces are not loaded by said forces and moments so that any deformations thereof can be safely and easily prevented or at least reduced. As a result, the electrodes usually being made from expensive material can have smaller dimensions than in the case of prior art instruments. The load-bearing structure absorbing forces and moments and, resp., the grip faces may be made, in the respective required dimension, from inexpensive material such as (thermoplastic) resin or ceramic.

In the case of electrode faces which are spaced apart or separated from each other merely locally by non-conductive spacers, as they are known from prior art, there is frequently the risk that with an appropriately high clamping force the instrument branches will deflect between the spacers and short-circuit will occur between the opposite electrodes. In contrast to this, in the configuration according to the invention the opposite electrode faces cannot contact each other, even if, in the ease of high clamping force, the two instrument branches are flatly adjacent to each other with their electrically non-conductive grip faces, as they are sunk in the grip face at least at one instrument branch. In this way, also better plane parallelism of the grip faces and thus also of the opposite electrode faces will be achieved.

Advantageous embodiments of the invention shall be explained in detail hereinafter.

According to one embodiment of the invention, in the closed position the distance between opposite electrode faces of both instrument branches ranges from 20 µm to 200 µm, preferably from 40 µm to 170 µm, more preferred from 80 µm to 150 µm and especially preferred from 95 µm to 110 µm. Alternatively or additionally, the distance between the electrode face of an instrument branch and the grip face of said instrument branch may range from 10 µm to 100 µm, preferably from 10µ to 80 µm, more preferred from 10 µm to 65 µm and especially preferred from 10 µm to 50 µm.

Especially simple handling for which the orientation of the instrument in the coagulation area does not matter can be achieved when the electrode faces of both instrument branches are arranged to be recessed at equal distance from the grip face of the respective instrument branch. However, it is also within the scope of the invention when the electrode faces are spaced differently far from the respective grip face. As an alternative, at least one electrode face of an instrument branch can be aligned with the grip face thereof, preferably can be flatly aligned, i.e. that the electrode faces and the grip face of one instrument branch are flush and, resp., are located in one plane. In this case, the corresponding opposite electrode face or the corresponding opposite electrode faces is/are arranged to be offset to the rear vis-à-vis the grip face of its/their instrument branch so that no short-circuit may occur.

According to an especially advantageous embodiment, at least one segment of a grip face is provided with a surface profile or a surface structure. According to a further development, at least areas opposing each other, at least segments, of the grip faces of both instrument branches are designed in this way. It may be of advantage when one of the grip faces, preferably both grip faces of the two instrument branches, is/are completely provided with such profile or structure. Safe clamping or retaining of tissue between the branches provided in the closed position can be effectuated by providing such surface profile/surface structure without high clamping pressure being required for this purpose, which is especially gentle for the tissue and helps to avoid collateral damage within the tissue.

According to another configuration of the invention, prevention of short circuit and clamping/retaining of tissue can be improved in that one of the electrode faces, preferably each electrode face, at least of one instrument branch, preferably of both branches, is fully surrounded, at least on both longitudinal sides with the short sides being free, by the grip face of the dedicated instrument branch. It can be ensured in this way that with a slight deformation of the instrument branches no mutual contact of the electrode faces and thus no short-circuits will occur. Especially the grip faces may be configured to have a rim peripheral on the facing sides of the instrument branches, preferably a continuously peripheral rim.

Another improvement of a safe and reproducible spacing of the electrode faces from each other as well as of the stability of the branches is achieved by the fact that the grip faces are in the form of a net-like matrix or perforated plate having insulating grip face lands and gaps located therebetween and exposing the electrode faces.

According to one aspect of the invention, the electrode faces may originate from a plurality of independent and possibly independently controllable electrodes or from one single coherent electrode whose electrode faces are exposed by recesses in the grip face provided at predetermined positions.

According to one embodiment of the invention, the grip face is configured, especially in one piece, at or by a supporting structure. Preferably the latter is made from electrically insulating material. In this way, the grip face can be manufactured especially easily, as no longer individual spacers have to be provided or applied to the electrodes. In one development, at least one of the instrument branches may include an electrically insulating outer housing which is formed in one piece with the grip face of the instrument branch. It is especially within the scope of the invention that an afore-mentioned supporting structure is in the form of such housing. The supporting structure or the housing completely surrounds the respective electrode forming the electrode face(s) except for the electrode face(s), i.e. shields it against the environment in all other spatial directions in an insulating manner.

An instrument according to the invention can be manufactured especially easily and inexpensively and can be durable and robust in that the electrode faces are configured by an electrode embedded in the housing by means of 2K-CIM technology, with the non-conductive part, the housing, being made from ceramics, e.g. $Al_2O_3$, and the electrode being made from electrically conductive mixed ceramics, e.g. $Al_2O_3$+TiN.

BRIEF DESCRIPTION OF THE DRAWINGS FIGURES

Further features and advantages of the present invention will be evident from the following exemplary and non-limiting description of the invention by way of figures. The latter are merely schematic and only serve for the comprehension of the invention, wherein:

FIG. 1 shows a section of an instrument according to the invention in a schematic lateral view, FIG. 2 shows a top view onto a clamping side of an instrument jaw part of the instrument of FIG. 1.

FIG. 3 shows a lateral view of the instrument jaw part of FIG. 2, and

FIG. 4 shows a sectional view along the line 4-4 in FIG. 2.

DETAILED DESCRIPTION

FIGS. 1 to 4 illustrate a jaw part 2 of an instrument 1 according to an embodiment of the invention. The jaw part 2 includes a first instrument branch 3 and a second instrument branch 4. The first instrument branch 3 is formed in one piece with an instrument body 5 indicated in FIG. 1 and is arranged thereon to be not movable relative thereto. The second instrument branch 4 is articulated to the instrument body 5 or to the first instrument branch 3 by means of a joint 6 or hinge 6. The second instrument branch 4 therefore can be pivoted about the joint 6 relative to the first instrument branch 3 between an opened position shown in FIG. 1 and a closed position not shown in the Figures in which the instrument branches 3, 4 are flatly adjacent to each other.

Both instrument branches 3, 4 have facing inner surfaces 7 and 8. Between the latter and, thus, between the instrument branches 3, 4 a clearance 9 is formed into which tissue to be coagulated by means of the instrument 1 is introduced.

The first instrument branch 3 includes a first electrode 10 and the second instrument branch 4 includes a second electrode 11. On the side facing the clearance 9 (inner surfaces 7, 8) the first electrode 10 has a first electrode face 12 and the second electrode 11 has a second electrode face 13. HF current has to be applied to the first and second electrodes 10, 11 by means of an electric circuitry not shown in the Figures and accommodated in the instrument body 5. For coagulating tissue, the two instrument branches 3, 4 are transferred from the opened position shown in FIG. 1 to a closed position not shown in the Figures and HF current is applied to them.

On the side facing the clearance 9 and thus the opposite instrument branch 4, a first grip face 14 is formed on the instrument branch 3. Correspondingly, on the side facing the clearance 9 and thus the opposite instrument branch 3, a second grip face 15 is formed on the instrument branch 4. As is evident especially from a combined consideration of the FIGS. 2 and 4, the first grip face 14 is formed of numerous partial grip faces or grip face segments. On the one hand, it has an externally peripheral grip face rim portion 16 and, on the other hand, a grip face matrix 17 formed inside the grip face rim portion 16. Said grip face matrix substantially consists of grip face lands 18 between which clearances 19 are formed for exposing, instead of covering, the electrode faces 12. The grip faces 14, 15 form contact areas by which the branches 3, 4 contact tissue and, possibly, the opposite branch 3, 4. The grip faces 14, 15 are electrically insulating.

FIG. 4 illustrates that the first electrode face 12 is arranged inside the first grip face 14 and is countersunk relative thereto. The first electrode face 12 thus is arranged or configured to be recessed vis-à-vis the first grip face 14 of the first instrument branch 3. It is offset to a direction facing away from the opposite second instrument branch 4. The offset of the first electrode face 12 vis-à-vis the first grip face 14 is marked in FIG. 4 by means of the partial gap height $H_1$. The second electrode face 13 and the second grip face 15 of the second instrument branch 4 can be correspondingly designed. In FIG. 4 the offset of the second electrode face 13 vis-à-vis the second grip face 15 is marked by means of the partial gap height $H_2$. When the jaw part 1 is so closed, the partial gap heights $H_1$ and $H_2$ add up to the gap height H between the electrode faces 12, 13.

FIG. 4 further illustrates that first grip face 14 is formed on the side facing the second instrument branch 4 of a housing structure 20 consisting of electrically insulating material. The first electrode 10 is accommodated inside the housing structure 20 in the afore-described manner, especially is cast or injected into the housing structure 20 by means of a 2K process. On the one hand, the housing structure 20 forms an electric, insulation surrounding each of the electrodes 10, 11 and, on the other hand, a spacer preventing the two electrodes 10, 11 from contacting each other. The configuration according to the invention allows the electrodes 10, 11 to be arranged in or at a load-bearing structure or to be retained by the same which absorbs forces and moments introduced by the tissue to be coagulated and transmits them into the instrument body 5 without those forces and moments being capable of causing an deformation of the electrodes 10, 11.

The invention claimed is:

1. An electrosurgical instrument for the electrocoagulation of tissue comprising:
   a first instrument branch comprising a first electrode; and
   a second instrument branch comprising a second electrode,
   the second instrument branch movable on a hinge relative to the first instrument branch between an opened position and a closed position,
   the first instrument branch and the second instrument branch being operable to clamp and hold tissue in the closed position for electrocoagulation of tissue,
   the first instrument branch comprising a flat perforated plate formed of electrically insulating material,
   the perforated plate defining a plurality of apertures arranged in a grid, the grid comprising a plurality of rows, wherein each row comprises two or more of said plurality of apertures,
   the perforated plate further comprising lands that surround each of the plurality of apertures and that form a grip face configured to contact tissue,
   the perforated plate positioned over the first electrode so that the first electrode is recessed in the first instrument branch under the perforated plate, with the first electrode being partially covered by the lands and partially exposed through the plurality of apertures,
   the first instrument branch comprising a proximal end extending toward the hinge, a distal end opposite the proximal end, and two sides extending longitudinally between the proximal end and the distal end,
   the first instrument branch defining a longitudinal axis extending from the proximal end to the distal end and centered between the two sides,
   at least one of the plurality of rows of apertures centered between the two sides and extending parallel to the longitudinal axis to expose the first electrode through the perforated plate along the longitudinal axis.

2. The electrosurgical instrument according to claim 1, wherein a distance between the first electrode and the second electrode in the closed position ranges from 20 μm to 200 μm, and/or a distance between the first electrode and the grip face ranges from 10 μm to 100 μm.

3. The electrosurgical instrument according to claim 1, wherein the first electrode and the second electrode are arranged to be equally recessed in the first instrument branch and the second instrument branch, respectively.

4. The electrosurgical instrument according to claim 1, wherein the second electrode comprises a second electrode face that is aligned with a second grip face of the second instrument branch.

5. The electrosurgical instrument according to claim 1, wherein at least one segment of the grip face is provided with a surface profile or a surface structure.

6. The electrosurgical instrument according to claim 1, wherein the first electrode comprises a first electrode face, the first electrode face being fully surrounded by the grip face.

7. The electrosurgical instrument according to claim 1, wherein the first instrument branch includes an electrically insulating outer housing which is formed in one piece with the grip face.

8. The electrosurgical instrument according to claim 1, wherein the grip face comprises a grip face rim portion which is peripheral on a side of the first instrument branch that faces the second instrument branch.

9. The electrosurgical instrument according to claim 1 further comprising a housing around the first instrument branch, wherein the first electrode is embedded in the housing by 2K-CIM technology.

10. The electrosurgical instrument according to claim 1, wherein the first electrode comprises a plurality of electrode faces exposed through the apertures, and wherein each of said plurality of electrode faces has a perimeter completely surrounded by the grip plate.

11. The electrosurgical instrument according to claim 10, wherein, each of the plurality of electrode faces is rectangular and surrounded on four sides by the perforated plate.

12. The electrosurgical instrument according to claim 10, wherein the perforated plate is bounded by an outer perimeter, and the outer perimeter is enclosed by a grip face rim portion.

13. The electrosurgical instrument according to claim 12, wherein the plurality of electrode faces are separate and insulated from the grip face rim portion by the perforated plate.

14. The electrosurgical instrument according to claim 1, wherein the first instrument branch further comprises a peripheral rim portion that forms a boundary around the grip face.

15. The electrosurgical instrument according to claim 1, wherein the second instrument branch comprises a second perforated plate formed of electrically insulating material, the second perforated plate defining a second plurality of apertures arranged in a second grid.

16. The electrosurgical instrument according to claim 15, wherein the second grid comprises a second plurality of rows, wherein each of the second plurality of rows comprises two or more of said second plurality of apertures.

17. The electrosurgical instrument according to claim 15, wherein the second perforated plate comprises second lands that surround each of the second plurality of apertures and form a second grip face configured to contact tissue.

18. The electrosurgical instrument according to claim 15, wherein the second perforated plate is positioned over the second electrode so that the second electrode is recessed in the second instrument branch behind the second perforated plate, with the second electrode being partially covered by the second lands and partially exposed through the second plurality of apertures.

19. The electrosurgical instrument according to claim 1, wherein the first electrode consists of a single unitary electrode comprising a first section covered by the perforated plate and a second section exposed through the plurality of apertures.

20. The electrosurgical instrument according to claim 19, wherein the perforated plate and the first section of the first electrode covered by the perforated plate define a matrix shape.

* * * * *